United States Patent [19]

Sugaya

[11] Patent Number: 4,800,762

[45] Date of Patent: Jan. 31, 1989

[54] LIQUID DEPOSITING DEVICE

[75] Inventor: Fumio Sugaya, Saitama, Japan

[73] Assignee: Fuji Photo Film Co., Ltd., Kanagawa, Japan

[21] Appl. No.: 62,874

[22] Filed: Jun. 16, 1987

[30] Foreign Application Priority Data

Jun. 20, 1986 [JP]  Japan ................................ 61-144258

[51] Int. Cl.$^4$ .............................................. G01N 1/14
[52] U.S. Cl. .................................. 73/864.24; 141/130
[58] Field of Search ........... 73/864.24, 864.25, 864.11, 73/864.13; 141/130

[56] References Cited

U.S. PATENT DOCUMENTS

| | | | |
|---|---|---|---|
| 3,449,959 | 6/1969 | Grimshaw | 73/864.24 |
| 3,635,094 | 1/1972 | Oberli | 73/864.24 X |
| 3,748,907 | 7/1973 | Sahmel | 73/864.24 |
| 3,853,008 | 12/1974 | Hoffa et al. | 73/864.25 X |
| 3,858,450 | 1/1975 | Jones | 73/864.24 X |
| 4,555,957 | 12/1985 | Frankel et al. | 73/864.25 X |
| 4,570,495 | 2/1986 | Terada | 73/864.25 |
| 4,598,596 | 7/1986 | Wiseman et al. | 73/864.25 X |

FOREIGN PATENT DOCUMENTS 61-231463  10/1986  Japan .

Primary Examiner—Werner H. Schroeder
Attorney, Agent, or Firm—Jules E. Goldberg

[57] ABSTRACT

A liquid depositing tip is removably mounted on a tip mounting portion formed on one end of a tip support arm mounted for up-and-down movement. A suction-and-discharge mechanism is operatively connected to the liquid depositing tip by way of the tip support arm to suck sample liquid into the depositing tip and to discharge the sucked sample liquid from the depositing tip onto a chemical assay slide. The quantity of the sample liquid to be sucked into the tip and to be discharged therefrom is controlled by a quantity control mechanism which controls the operation of the suction-and-discharge mechanism. The tip support arm is adapted to be moved up and down between a sucking position in which mounting or removal of the depositing tip is effected, as required, and the sample liquid is sucked into the tip, and a depositing position in which the lower end of the tip is positioned immediately above the reagent layer of a chemical assay slide set to a predetermined position, the sucking position being higher than the depositing position.

7 Claims, 2 Drawing Sheets 4,800,762

LIQUID DEPOSITING DEVICE

BACKGROUND OF THE INVENTION

1. Field of the Invention

This invention relates to a liquid depositing device for automatically depositing a predetermined quantity of sample liquid in a sample container on a chemical assay slide bearing thereon a reagent layer.

1. Description of the Prior Art

Qualitative and/or quantitative determination of a particular chemical component in a liquid sample is widely used in various industrial fields. Especially, in the fields of biochemistry and clinical medicine, quantitative determination of a particular chemical component or particulate substance in body fluids such as blood or urine is extremely important.

Recently, there has been put into practice a dry type chemical assay slide by which a particular chemical component or material component in a liquid sample can be determined by depositing a droplet of the liquid sample on the slide. Japanese patent publication No. 53(1978)-21677, Japanese Unexamined patent publication No. 55(1980)-164356, for example, are referred to. By using such chemical assay slides, liquid samples can be assayed more easily and more quickly in comparison to the conventional wet analyzing process, and accordingly, the chemical assay slide is conveniently used in medical facilities, laboratories and the like where a large number of samples must be assayed.

When a liquid sample is assayed using the chemical assay slide, a measured quantity of the liquid sample is deposited on the slide and the slide is held in an incubator for a predetermined time at a constant temperature to permit reaction to cause coloration, and then light including a wavelength selected previously depending on the components of the liquid sample and the reagents contained in the reagent layers on the slide is projected onto the slide to measure the reflection density thereof.

The quantity of the sample liquid to be deposited on the slide must be measured with a high accuracy since the reflection density differs depending on the quantity of the sample liquid. Accordingly, there have been proposed various instruments such as a pipet for depositing the sample liquid with a high accuracy. For example, there has been known a pipet employing a piston/cylinder mechanism in which sample liquid is sucked into a tip mounted on the front end of the pipet by moving rearward the piston and then discharged from the tip to be deposited on a chemical assay slide by moving forward the piston.

However, such pipets are generally manually operated and are not suitable where a large number of samples must be assayed. Further, such a manually operated pipet is disadvantageous in that the quantity of the sample liquid which can be deposited at one time is fixed and accordingly the pipet must be changed according to the quantity of sample to be deposited. Though some of the known systems can automatically deposit sample liquid, the quantity of the sample liquid to be deposited cannot be freely controlled in any of the known systems.

SUMMARY OF THE INVENTION

In view of the foregoing observations and description, the primary object of the present invention is to provide a liquid depositing device in which a desired quantity of sample liquid can be automatically deposited on the chemical assay slide with a high accuracy and the quantity of the sample liquid to be deposited on the slide can be freely changed.

In the liquid depositing device in accordance with the present invention, a liquid depositing tip is removably mounted on a tip mounting portion formed on one end of a tip support arm mounted for up-and-down movement. A suction-and-discharge mechanism is operatively connected to the liquid depositing tip by way of the tip support arm to suck sample liquid into the depositing tip and to discharge the sucked simple liquid from the depositing tip onto a chemical assay slide. The quantity of the sample liquid to be sucked into the tip and to be discharged therefrom is controlled by a quantity control mechanism which controls the operation of the suction-and-discharge mechanism. The tip support arm is adapted to be moved up and down between a sucking position in which mounting or removal of the depositing tip is effected, as required, and the sample liquid is sucked into the tip, and a depositing position in which the lower end of the tip is positioned immediately above the reagent layer of a chemical assay slide set to a predetermined position, the sucking position being higher than the depositing position.

DESCRIPTION OF THE PREFERRED EMBODIMENT

Figure 4:
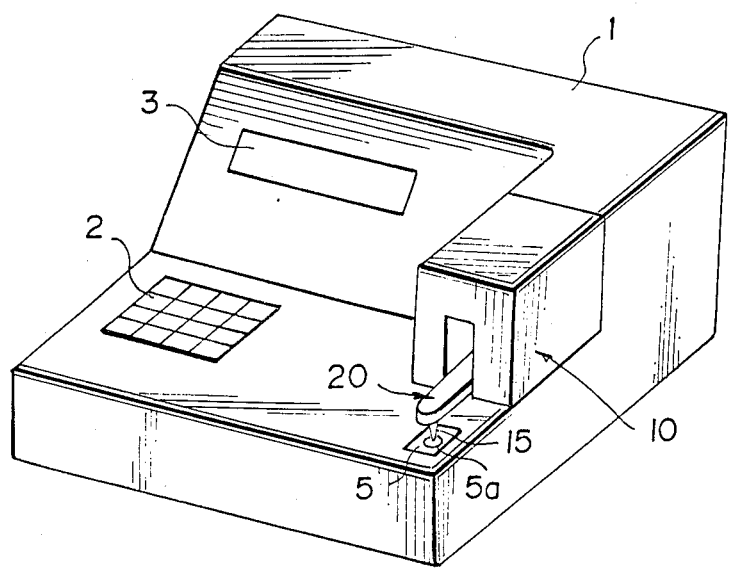
FIG. 4 is a perspective view showing a chemical assay system in which the liquid depositing device is employed.

FIG. 4 shows a chemical assay system provided with a liquid depositing device 10 in accordance with an embodiment of the present invention. The chemical assay system has a body 1 on which an input key board 2 and a display portion 3 are provided. The liquid depositing device 10 is mounted on the body 1. The display portion 3 is for displaying measurement data and the like, and the operation of the display portion 3 and the liquid depositing device 10 are controlled by operation of the input key board 2. The liquid depositing device 10 has an arm 20 projecting forward from the body for up-and-down swinging motion. A depositing tip 15 is removably mounted on the projecting end portion of the arm 20, and a chemical assay slide 5 having a reagent layer 5a is positioned on the body 1 below the depositing tip 15. The liquid depositing device 10 is for automatically depositing a predetermined quantity of sample liquid on the reagent layer 5a of the slide 5.

The liquid depositing device 10 will be described in detail with reference to FIGS. 1 and 2. The liquid depositing device 10 comprises the arm 20, a suction-and-discharge mechanism 30 and an arm swinging mechanism 50 disposed in a box casing 11, and a controller 40 disposed in the body 1 and connected with the body 1 by way of a connector 41. The box casing 11 is a rectangular box and is placed on the body 1 by way of an adjustable length leg 12a and a pair of fixed legs 12a and 12b. The box casing 11 is provided on the front face with a vertical slot 11a which permits the arm 20 to project forward and to be swung up and down.

The arm 20 comprises a base arm portion 22 pivotally mounted on the bottom of the box casing 11 by way of a pin 22a, and a front arm portion 21 fixed to the front end of the base arm portion 22 to project forward through the vertical slot 11a. On the front end of the front arm portion 21 is formed a tip mounting portion 21b to extend downward. The depositing tip 15 is provided with an inner space 15b and a suction-and-discharge port 15a communicated with the inner space 15b and is removably mounted on the tip mounting portion 21b. A sample liquid passage 21a is formed in the front arm portion 21 and is communicated with the inner space 15b of the depositing tip 15. The arm 20 is adapted to be swung up and down (as indicated at arrow A) about the pin 22a with the depositing tip 15 mounted on the tip mounting portion 21b.

The suction-and-discharge mechanism 30 comprises a piston 31 fit into the rear end portion of the sample liquid passage 21a to be slidable back and forth, a first driven gear 32 having a female thread in engagement with a male thread 31a formed on the rear end portion of the piston 31 and supported for rotation on the base arm portion 22, a first pinion 33 in mesh with the first driven gear 32, and a first pulse motor 34 for driving the first pinion 33. When the first pulse motor 34 is energized, the first driven gear 32 is rotated by way of the first pinion 33 and the piston 31 is slid back and forth by way of the engagement of the male thread 31a on the piston 31 and the female thread on the first driven gear 32, whereby sample liquid can be sucked into the inner space 15b of the depositing tip 15 and the sample liquid sucked into the inner space 15b can be discharged through the suction-and-discharge port 15a to be deposited on the reagent layer 5 of the slide 5.

The arm swinging mechanism 50 comprises a sector gear 51 fixed to the base arm portion 22 coaxially with the pin 22a, a second pinion 52 in mesh with the sector gear 51, and a second pulse motor 53 for driving the second pinion 52. When the second pinion 52 is rotated by the second pulse motor 53, the sector gear 51 is swung about the pin 22a. Since the sector gear 51 is fixed to the base arm portion 22, the base arm portion 22 is swung along with the sector gear 51 about the pin 22a, whereby the arm 20 is swung in the direction of the arrow A.

The controller 40 controls the first pulse motor 34 to control the quantity of sample liquid to be sucked into the depositing tip 15 and the quantity of sample liquid to be discharged from the tip 15. Further, the controller 40 controls the second pulse motor 53 to swing the arm 20.

Figure 3:
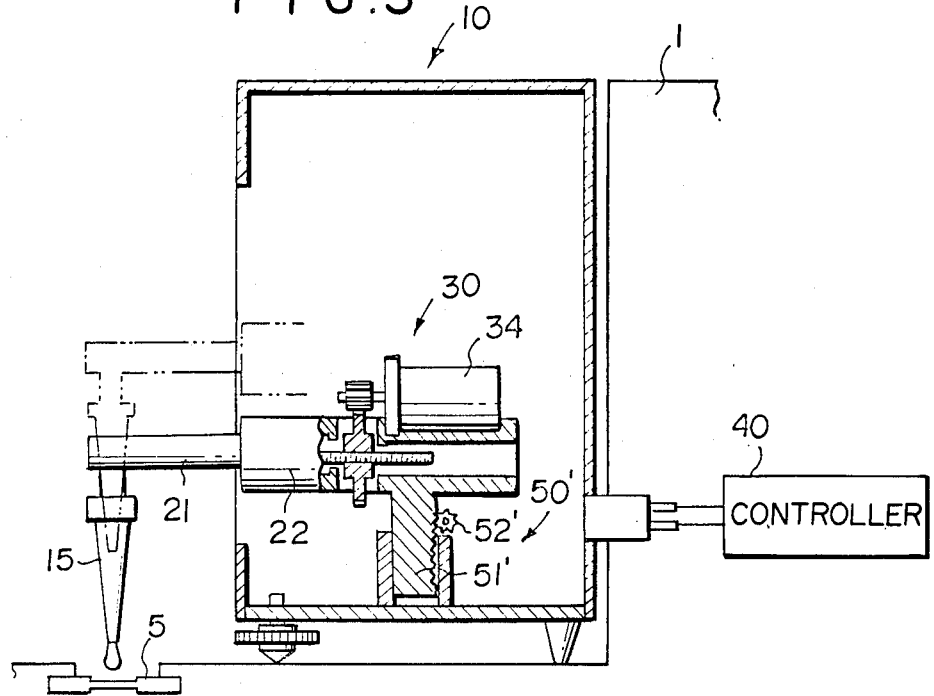
FIG. 3 is a cross-sectional view of a modification of the liquid depositing device shown in FIGS. 1 and 2.

Instead of being swung up and down, the arm 20 may be linearly slid up and down by means of an arm lift mechanism 50' comprising a vertical rack 51' fixed to the base arm portion 22, a pinion 52' in mesh with the rack 51' and a pulse motor (not shown) for driving the pinion 52' as shown in FIG. 3.

Figure 1:
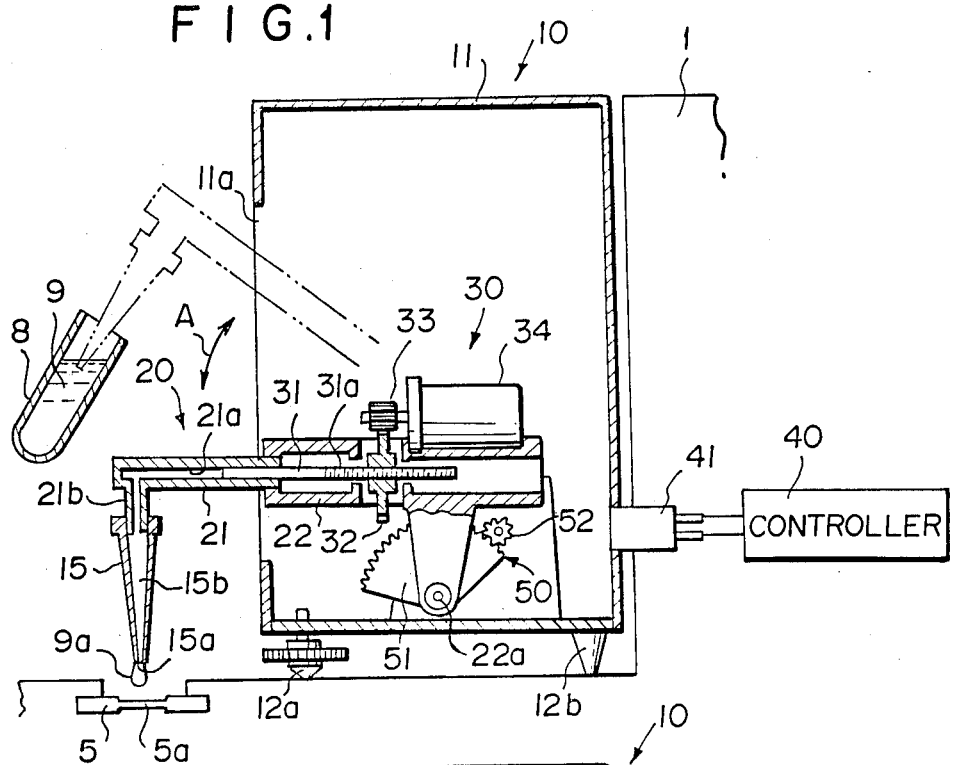
FIG. 1 is a cross-sectional view of a liquid depositing device in accordance with an embodiment of the preset invention.
Figure 2:
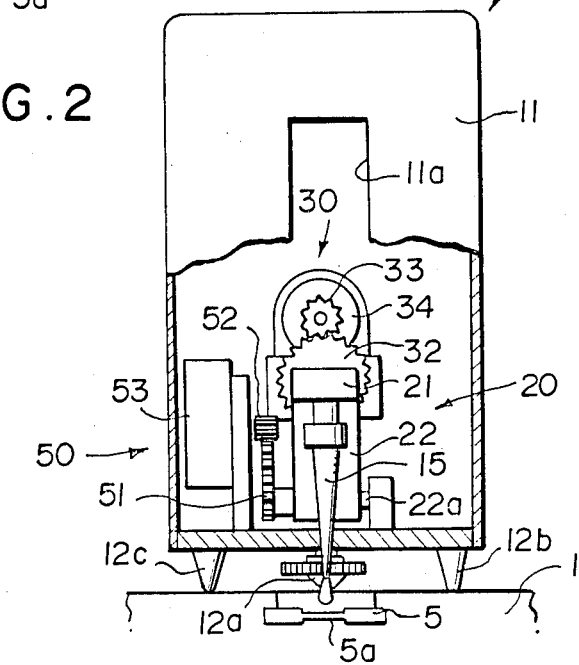
FIG. 2 is a front view partly broken away of the liquid depositing device.

When operating the liquid depositing device 10 of this embodiment, the second pulse motor 53 is first driven to swing upward the arm 20 about the pin 22a to the sucking position shown by the chained line in FIG. 1. In the sucking position, a new tip 15 is mounted on the tip mounting portion 22b. Then a sample container 8 containing therein sample liquid 8 is manually applied to the depositing tip 15 to dip the lower end portion of the depositing tip into the sample liquid 8. Then the first pulse motor 34 is driven to move rearward the piston 31 by a predetermined distance, thereby sucking the sample liquid 8 into the inner space 15b of the depositing tip 15 by a desired quantity. Then the second pulse motor 53 is driven to return the arm 20 to the depositing position shown by the solid line in FIG. 1.

In the depositing position, the port 15a of the depositing tip 15 is positioned immediately above the reagent layer 5a of the chemical assay slide 5 placed on the slide setting portion of the body 1. Accordingly, by driving the first pulse motor 34 in the reverse direction to move forward the piston 31, the sample liquid 9 held in the inner space 15b of the tip 15 can be deposited on the reagent layer 5a of the chemical assay slide 5. It is preferred that the sample liquid 9 be deposited on the reagent layer 5a by first forming a drop of a predetermined quantity of the sample liquid 9 on the lower end of the depositing tip 15 and then further lowering the depositing tip 15 to bring the drop of the sample liquid 9 into contact with the reagent layer 5a.

By controlling the first and second pulse motors 34 and 53 in the manner described above, the sample liquid 9 is sucked into the depositing tip 15 and deposited on the reagent layer 15a. Such control of the pulse motors 34 and 53 is accomplished by a control signal delivered from the controller 40 by way of the connector 41, and the controller 40 can be operated by operation of the key board 2.

By controlling rotation of the first pulse motor 34 by way of the controller 40, the quantity of the sample liquid to be sucked into the depositing tip 15 and the quantity of the same to be discharged from the depositing tip 15 can be freely controlled. Since the quantity of the sample liquid to be sucked into and discharged from the depositing tip 15 is generally determined depending on the kind of the slide 5 and the like, it is preferred that the quantity of the sample liquid be automatically determined by the chemical assay system by reading a bar code or the like provided on the chemical assay slide 5 to indicate the quantity of the sample liquid to be deposited on the specific slide though information about the quantity of the sample liquid may be manually input into the controller 40 by way of the key board 2.

I claim:
1. A liquid depositing device comprising,
   a liquid depositing tip for sucking sample liquid in a container through a lower end thereof and depositing the sucked sample liquid on a chemical assay slide,
   a tip support arm mounted for up-and-down movement and provided with a tip mounting portion on which said liquid depositing tip is removably mounted,
   a suction-and-discharge means operatively connected to said liquid depositing tip by way of said tip support arm to suck sample liquid into said liquid depositing tip and to discharge the sucked sample liquid from said depositing tip onto the chemical assay slide,
   a quantity control means which controls the operation of said suction-and-discharge means to control the quantity of the sample liquid to be sucked into said liquid depositing tip and to be discharged therefrom, and
   an arm driving means for moving said tip support arm up and down between a sucking position in which mounting or removal of the tip is effected and the sample liquid is sucked into the tip, and a deposit- ing position in which the lower end of the tip is positioned immediately above a chemical assay slide, the sucking position being higher than the depositing position.

2. A liquid depositing device as defined in claim 1 in which said tip support arm is adapted to be swung up and down between the sucking position and the depositing position by the arm driving means.

3. A liquid depositing device as defined in claim 1 in which said quantity control means is a pulse motor which drives said suction-and-discharge means.

4. A liquid depositing device as defined in claim 3 in which said pulse motor is controlled by a control signal.

5. A liquid depositing device as defined in claim 4 in which said control signal is generated by a controller.

6. The device of claim 1 wherein said tip is pivotably mounted for radial movement between said sucking and depositing positions.

7. The device of claim 1 wherein said tip is mounted for linear vertical movement between said sucking and depositing positions.

* * * * *